US009750682B2

(12) United States Patent
Pernodet et al.

(10) Patent No.: US 9,750,682 B2
(45) Date of Patent: Sep. 5, 2017

(54) METHODS AND COMPOSITIONS FOR IMPROVING THE APPEARANCE OF SKIN (71) Applicant: ELC Management LLC, Melville, NY (US)

(72) Inventors: Nadine Pernodet, Huntington Station, NY (US); Donald Collins, Plainview, NY (US)

(73) Assignee: ELC Management, LLC, Melville, NY (US)

( * ) Notice: Subject to any disclaimer, the term of this patent is extended or adjusted under 35 U.S.C. 154(b) by 132 days.

(21) Appl. No.: 14/813,212

(22) Filed: Jul. 30, 2015

(65) Prior Publication Data
US 2017/0027854 A1 Feb. 2, 2017

(51) Int. Cl.
*A61K 36/00* (2006.01)
*A61K 8/97* (2017.01)
*A61K 8/66* (2006.01)
*A61Q 19/08* (2006.01)

(52) U.S. Cl.
CPC ............. *A61K 8/975* (2013.01); *A61K 8/66* (2013.01); *A61K 8/97* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 3,215,724 A | 11/1965 | Strobel et al. | |
| 3,781,417 A | 12/1973 | Welters et al. | |
| 4,970,252 A | 11/1990 | Sakuta et al. | |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 6,051,212 A | 4/2000 | Kado et al. | |
| 6,635,287 B2 | 10/2003 | Soudant et al. | |
| 2005/0226947 A1 | 10/2005 | Kern | |
| 2008/0175935 A1* | 7/2008 | Kern | A61K 8/355 424/773 |
| 2009/0246153 A1 | 10/2009 | Kern | |
| 2011/0070258 A1 | 3/2011 | Jimenez Del Rio et al. | |
| 2011/0318284 A1* | 12/2011 | Dal Farra | A61K 8/64 424/59 |
| 2012/0195923 A1* | 8/2012 | Turgeon | A61K 8/975 424/195.17 |

FOREIGN PATENT DOCUMENTS

| | | |
|---|---|---|
| JP | 61-18708 | 1/1986 |
| JP | 2008291004 | 12/2008 |
| JP | 2013531005 B2 | 8/2013 |
| KR | 20120026308 | 3/2012 |
| KR | 20130094043 | 8/2013 |
| WO | WO-2009/120214 | 10/2009 |
| WO | WO-2010/145008 | 12/2010 |

OTHER PUBLICATIONS

Berendsen, A Glimpse of the Holy Grail?, Science, 1998, 282, pp. 642-643.
Bradley, et al.; Limits of Cooperativity in a Structurally Modular Protein: Response of the Notch Ankyrin Domain to Analogous Alanine Substitutions in Each Repeat, J. Mol. BioL (2002) 324, 373-386.
English translation of Estee Lauder—Revitalizing Supreme Global Anti-Aging Creme, pp. 1-6, accessed May 2014.
Estee Lauder Re-Nutriv Ultimate Lifting Age Correction, from http://londonprettyboy.wordpress.com/tag/age-correction/, pp. 1-7, published on Dec. 3, 2010.
Estee Lauder Revitalizing Supreme Global Anti-Aging Creme-Product Study, from http://www.cosmetoscope.com/2012/02/estee-lauder-revitalizing-supreme-global-anti-aging-cream-product-study/, pp. 1-5, published on Feb. 29, 2012.
Estee Lauder—Revitalizing Supreme Global Anti-Aging Creme, from http://www.cosmoty.de/news/4793/, pp. 1-2, published on Jan. 2012.
Estee Lauder's Re-Nutriv Ultimate Lift Age-Correcting Creme with Most Effective Skin Restoring Ingredients, from http://www.specialchem4cosmetics.com/services/news.aspx?id=5799, p. 1, published on Nov. 10, 2010.
Glycerol, from http://www.naturalwellbeing.com/learning-center/Glycerol, pp. 1-3, accessed Apr. 24, 2014.
http://www.gnpd.com; Mintel GNPD; Resilience Lift Firming/Sculpting; Record ID: 1690377; Estee Lauder; Skincare; Eye Care; China; Dec. 2011.
Laminaria Review, from http://www.dietspotlight.com/laminaria-review/, pp. 1-4, accessed May 13, 2014.
NAD-dependent protein deacylase sirtuin-5-mitochondrial-Mus Musculus, from http://www.ncbi.nlm.nih.gov/protein/NP_849179.1, pp. 1-3, accessed May 13, 2014.
Narcissus extract, from http://blog.tataharperskincare.com/slowing-the-aging-process-with-narcissus/, pp. 1-4, accessed May 13, 2014.
Ngo, et al.; Computational Complexity, Protein Structure Protection, and the Levinthal Paradox, 1994, pp. 491-494.
PCT International Search Report; International Application No. PCT/US2014/058650; Completion dated Jan. 14, 2015; dated Jan. 14, 2015.
PCT Written Opinion of the International Searching Authority; International Application No. PCT/US2014/058650; Completion dated Jan. 14, 2015; dated Jan. 14, 2015.
Rudinger, Peptide Hormones, JA Parsons, Ed., 1976, pp. 1-7.
Schiener, et al.; The seasonal variation in the Chemical Composition of hte Kelp Speciies *Laminaria digitata, Laminaria hyperborea, Saccharina latissima* and *Alaria esculenta*; J. Appl Phycol, 2014; pp. 1-11.

(Continued)

Primary Examiner — Qiuwen Mi
(74) Attorney, Agent, or Firm — Julie Blackburn (57) ABSTRACT A method for stimulating collagen synthesis in aging skin cells in need of treatment by stimulating SIRT1, SIRT3, and SIRT6 and a method for preparing a topical composition for stimulating SIRT1, SIRT3, and SIRT6 in skin cells.

14 Claims, 3 Drawing Sheets

(56) References Cited

OTHER PUBLICATIONS

SIGMA, 2004, pp. 1-2.
Tallarida, Ronald J.; Drug Synergism and Dose-Effect Data Analysis; CRC Press LLC, 2000; pp. 1-29.
Voet, et al.; Biochemistry; John Wiley & Sons Inc., 1995, pp. 235-241.
Water, from http://www.biology-online.org/dictionary/Water, pp. 1-3, accessed Apr. 24, 2014.
Yeast extract, from http://www.yeastextract.info/faq, pp. 1-4, accessed May 13, 2014.
Supplemental European Search Report; EP14850636; dated Feb. 7, 2017; Completion dated Jan. 30, 2017.

* cited by examiner

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: Amidation

<400> SEQUENCE: 1

Glu Ile His Gly Ser Leu Phe Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (6)..(6)
<223> OTHER INFORMATION: Amidation

<400> SEQUENCE: 2

His Gly Ser Leu Phe Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: Amidation

<400> SEQUENCE: 3

Leu Val Gly Ala Gly Val Ser Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4
```

Gly Ala Gly Val Ser Ala Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: Amidation

<400> SEQUENCE: 5

Gly Ala Gly Val Ser Ala Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Thr Gln Asn Ile Asp Glu Leu
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: Amidation

<400> SEQUENCE: 7

Thr Gln Asn Ile Asp Glu Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: Amidation

<400> SEQUENCE: 8

Val Ile Thr Gln Asn Ile Asp Ala
1               5

METHODS AND COMPOSITIONS FOR IMPROVING THE APPEARANCE OF SKIN

TECHNICAL FIELD

The invention is in the field of methods and compositions for improving the appearance of aging skin, and more specifically reducing laxity and/or wrinkles or fine lines by, among other things, enhancing collagen synthesis in skin cells.

BACKGROUND OF THE INVENTION

Sirtuins are enzymes that play critical roles in many cellular epigenetic or metabolic pathways. In mammalian cells seven sirtuin homologs have been identified, referred to as SIRTUINS 1-7 or SIRT1-7. SIRT1 and SIRT6 are localized in the cell nucleus. SIRT3, SIRT4, and SIRT5 are found in the mitochondria. SIRT2 is found in the cytoplasm and SIRT7 in the nucleolus.

The invention is directed to a method and compositions that have anti-aging effects, in particular by activating sirtuins, which in turn promote collagen synthesis, improve the appearance of lines and wrinkles, and exert other beneficial effects on skin cells. The composition of the invention comprise a method for stimulating collagen synthesis in aging skin cells that are in need of treatment by topically applying a composition comprising at least one extract from *Laminaria* genus, at least one extract from the *Narcissus* genus, and at least one peptide that stimulates SIRT6 activity.

DETAILED DESCRIPTION

All percentages mentioned herein are percentages by weight unless otherwise indicated.

The Extract from *Laminaria* Genus

The composition used in the method of the invention contains at least one extract from the *Laminaria* genus. *Laminaria* is a genus that contains 30+ species of the brown algae Phaeophyceae, often referred to as kelp. Such extracts from the *Laminaria* genus include those of species *abyssalis, agardhii, appressirhiza, brasiliensis, brongardiana, bulbosa, bullata, complanata, digitata, ephemera, farlowii, groenlandica, hyperborea, inclinitorhiza, multiplicata, nigripes, ochroleuca, pallida, platymeris, rodriguezi, ruprechtii, sachalinensis, setchellii, sinclairii, solidungula,* or *yezoensis*. Preferred is where the extract from the *Laminaria* genus is also a SIRT3 activator. Preferred is where the extract is from *Laminaria digitata*, and more specifically an extract having laminarin content and/or a mannitol content of 1% by weight or greater, preferably around 2%. An example of a suitable extract of *Laminaria digitata* may be purchased from Barnet Products under the tradename Mitostime™ Di which is a mixture of 91 parts water, 8 parts *Laminaria digitata* extract, and 1 part preservative. Preferably the *Laminaria digitata* extract is obtained by aqueous extraction and leaching of lyophilized algae and sterilizing the microfiltration, followed by reverse osmosis to concentrate the active molecules.

In the preferred embodiment of the invention the extract may be present in the composition in amounts ranging from 0.0001 to 5%, preferably from about 0.001 to 2.5%, more preferably from about 0.01 to 1%. In a more preferred embodiment of the invention the extract is a SIRT3 expression activator, particularly in keratinocytes.

The Extract from *Narcissus* Genus

The composition used in the method also contains at least one extract from the *Narcissus* genus. Preferably the extract is a SIRT1 activator. Suggested ranges are from about 0.001 to 5%, preferably from about 0.01-4%, more preferably from about 0.05 to 1.5%. Examples of extracts include those from species *alcaracensis, assoanus, asturiensis, bugei, bulbocodium, cyclamineus, jonquilla, longispathis, papyraceus, poeticus, pseudonarcissus, radingnaorum, romeiuxii, tazetta, triandrus,* or *medioluteus*. More preferred is an extract from *Narcissus tazetta*, and in particular, an extract from the bulb when it is in the dormant state. Most preferred is *Narcissus tazetta* bulb extract purchased from IBR Dormin which is a mixture of about 62.5 parts glycerin, 37 parts water, and 0.5 parts *Narcissus tazetta* bulb extract. The extract may be prepared as set forth in U.S. Pat. No. 6,635,287, hereby incorporated by reference in its entirety. In particular, the extract may be prepared by inducing dormancy in *Narcissus* bulbs by storing at temperatures around 45° C. for 2-24 hours. Water soluble extracts are then prepared by washing and disinfecting the bulbs, then cutting and homogenizing in distilled water. The resulting mass is then filtered to provide a liquid filtrate that contains the extract. In a most preferred embodiment of the invention the *Narcissus* extract is an activator of SIRT1 in keratinocytes.

SIRT6 Activating Peptide

The composition also contains at least one peptide that is an activator of SIRT6. Such peptides are taught in U.S. patent application No. 2011/0318284 which is hereby incorporated by reference in its entirety. Such peptides have the general formula:

$$R_1\text{-}(AA)_n\text{-}X_1\text{-}X_2\text{-}X_3\text{-}X_4\text{-}X_5\text{-}X_6\text{-}(AA)_p\text{-}R_2 \qquad (I)$$

in which, $X_1$ is glycine or threonine or histidine;

$X_2$ is alanine or glutamine or glycine;

$X_3$ is glycine or asparagine or serine;

$X_4$ is valine or isoleucine or leucine;

$X_5$ is serine or aspartic acid or phenylalanine;

$X_6$ is alanine or glutamic acid or lysine;

and when $X_1$ is glycine then $X_2$ is alanine and $X_3$ is glycine;

when $X_1$ is threonine then $X_3$ is asparagine;

when $X_1$ is histidine then $X_2$ is glycine;

AA represents any amino acid and n and p are integers between 0 and 2;

$R_1$ represents the primary amino function of the N-terminal amino acid, free or substituted by an acyl type group having either an alkyl chain from $C_{1\text{-}30}$, saturated or unsaturated, that may be an acetyl group, or an aromatic group that may be chosen from among a benzoyl, tosyl or benzyloxycarbonyl type group; and $R_2$ represents the hydroxyl group of the carboxyl function of the C-terminal amino acid, free or substituted by a group that may be chosen from among an alkyl chain from C1-30, or an $NH_2$, NHY or NYY group with Y representing an alkyl chain from C1-4.

More preferred are peptides corresponding to the following:

(SEQ ID No. 1): Glu-Ile-His-Gly-Ser-Leu-Phe-Lys-$NH_2$
(SEQ ID No. 2)  His-Gly-Ser-Leu-Phe-Lys-$NH_2$
(SEQ ID No. 3)  Leu-Val-Gly-Ala-Gly-Val-Ser-Ala-$NH_2$
(SEQ ID No. 4)  Gly-Ala-Gly-Val-Ser-Ala-Glu
(SEQ ID No. 5)  Gly-Ala-Gly-Val-Ser-Ala-Glu-$NH_2$
(SEQ ID No. 6)  Thr-Gln-Asn-Ile-Asp-Glu-Leu
(SEQ ID No. 7)  Thr-Gln-Asn-Ile-Asp-Glu-Leu-$NH_2$
(SEQ ID No. 8)  Val-Ile-Thr-Gln-Asn-Ile-Asp-Ala-$NH_2$

In one preferred embodiment, the peptides of SEQ ID No. 5 and 7 are preferred.

The SIRT6 activating peptide may be present in the composition in amounts ranging from 0.0001 to 8%, preferably from about 0.001 to 3%, more preferably from about 0.01 to 1%. The term "SIRT6 activating peptide" means a peptide that causes the amount of SIRT6 in the cell to increase by whatever pathway causes that result, and where the types of cells include keratinocytes, dermal fibroblasts, etc. Most preferred is the peptide having SEQ ID No. 5.

In another preferred embodiment, the peptide may be found as a component of an extract from yeast. In this case, the peptide may be present in the yeast extract composition in amounts ranging from 10 to 1,000,000 ppm, or from 100 to 100,000 ppm, or even from 1,000 to 10,000 ppm.

Other Ingredients

The composition of the invention may be in the liquid, semi-solid, or solid form, and may be in the emulsion, solution, suspension, or anhydrous form. If in the solution or suspension form, the composition may contain from about 50 to 99.9% water. If in the emulsion form, the composition may contain from about 5-95% water and from about 5-95% oil. If in the anhydrous form, the composition may comprise from about 10-99% oil and 10-99% solidifying agents.

Thickening Agents

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below.

Polysaccharides

Polysaccharides may be suitable aqueous phase thickening agents. Examples of such polysaccharides include naturally derived materials such as agar, agarose, *alicaligenes*polysaccharides, algin, alginic acid, *acacia* gum, amylopectin, chitin, dextran, *cassia* gum, cellulose gum, gelatin, gellan gum, hyaluronic acid, hydroxyethyl cellulose, methyl cellulose, ethyl cellulose, pectin, *sclerotium* gum, xanthan gum, pectin, trehelose, gelatin, and so on.

Acrylate Polymers

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

Oils

In the event the compositions of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature.

The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

Suitable volatile oils generally have a viscosity ranging from about 0.5 to 5 centistokes 25° C. and include linear silicones, cyclic silicones, paraffinic hydrocarbons, or mixtures thereof.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

Methyl trimethicone may be purchased from Shin-Etsu Silicones under the trade name TMF-1.5, having a viscosity of 1.5 centistokes at 25° C.

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to esters in the mono-, di-, or triester form.

Examples of monoesters include those formed by the reaction of a monocarboxylic acid and an alcohol. The alcohol and the carboxylic acids may both have fatty (C6-30) chains. Examples include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

The ester may also be in the dimer or trimer form. Examples of such esters include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Examples of other types of esters include those from arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Examples include dimethicone, phenyl dimethicone, diphenyl dimethicone, phenyl trimethicone, or trimethylsiloxyphenyl dimethicone. Other examples include alkyl dimethicones such as cetyl dimethicone, stearyl dimethicone, behenyl dimethicone, and the like.

Oil Phase Structuring Agents

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silsesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety. It is particularly desirable to incorporate silicone elastomers into the compositions of the invention because they provide excellent "feel" to the composition, are very stable in cosmetic formulations, and relatively inexpensive.

Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

Natural or Synthetic Organic Waxes

Also suitable as the oil phase structuring agent may be one or more natural or synthetic waxes such as animal, vegetable, or mineral waxes. Preferably such waxes will have a higher melting point such as from about 40 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, *acacia*, beeswax, ceresin, cetyl esters, flower wax, *citrus* wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

Silicas and Silicates

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Suitable silicone surfactants include:

Dimethicone Copolyols or Alkyl Dimethicone Copolyols

One type of suitable silicone surfactant has the general formula:

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

Another type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Crosslinked Silicone Surfactants

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. Nos. 5,236,986 and 5,412,004, 5,837,793 and 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. All recitations of units include all whole integers between the range.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *thermus thermophilis* ferment extract, camelina *sativa* seed oil, boswellia *serrata* extract, olive extract, *Aribodopsis Thaliana* extract, *Acacia Dealbata* extract, *Acer Saccharinum* (sugar maple), acidopholus, acorus, *aesculus, agaricus*, agave, agrimonia, algae, aloe, *citrus, brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sannentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum*, Bifida Ferment lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus*, Hordeum Vulgare, *Cucumis Sativus, Evernia Prunastri, Evemia Furfuracea*, and mixtures thereof.

Sunscreens

It may also be desirable to include one or more sunscreens in the compositions of the invention. Such sunscreens include chemical UVA or UVB sunscreens or physical sunscreens in the particulate form.

UVA Chemical Sunscreens

If desired, the composition may comprise one or more UVA sunscreens. The term "UVA sunscreen" means a chemical compound that blocks UV radiation in the wavelength range of about 320 to 400 nm.

Examples of suitable UVA sunscreen compounds include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the trade name Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives including Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Salicylate derivatives are also acceptable UVB absorbers. Such compounds have the general formula:

wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-100, preferably about 5-80, most preferably about 5-50%. Calculation of SPF values is well known in the art.

Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

Powders

The particulate matter may be colored or non-colored powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition may be free of parabens.

Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophosphate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythorbate, sodium metabisulfite, sodium sulfite, propyl gallate, cysteine hydrochloride, butylated hydroxytoluene, butylated hydroxyanisole, and so on.

The invention further comprises treating skin for improvement by applying to the skin the compositions of the invention. The compositions may be applied in the forms mentioned herein, as part of skin care regimens. For example, the composition may be applied to the skin as a night cream or cream applied to skin prior to a period of bodily rest such as a nap or sleep. The composition may be applied two times a day, in the morning and in the evening after cleansing the skin. The composition may be applied to the skin over skin care products, in the form of foundations or other color cosmetics.

The invention will be further described in connection with the following examples which are set forth for the purposes of illustration only.

EXAMPLE 1

*Laminaria digitata* extract, yeast extract composition with SIRT6 peptide, and *Narcissus tazetta* bulb extract were tested for collagen synthesis. Samples and reagents were prepared as follows:

Growth Media: 50 ml fetal bovine serum, 5 ml pen/strep solution was added to 445 ml Dulbecco's Modified Eagle Medium ("DMEM") (high glucose). The mixture was filtered through 0.22 um PES filtration system and stored at 2-8° C.

PBS (Phosphate Buffered Saline): 20 packets of PBS, pH 7.4, and 10 ml Tween 20 added to 800 ml DI water and mixed well. Solution was QS'ed to 1 liter with DI water, filtered through a 0.2 um PES filtration system and stored at room temperature.

Plate Wash: 500 ml PBS was mixed with 9.5 liters DI water, mixed well and stored at room temperature.

Cell Cultures: Normal Human Dermal Fibroblasts (NHDF) were grown to confluence in a T-75 flask. One confluent T-75 flask was trypsinized. A 24 ml resuspension of 60,000 cells per ml was resuspended in Growth Media. 200 ul per well was dispensed into a 96 well plate. Cells were grown to 100% confluence (about 1 day). When confluence was reached the spent media was aspirated and 200 ul per well of fresh media was added.

Positive Control: A PIP positive control was prepared by treating cells with ascorbic acid at a final concentration of 18 ug/ml in triplicate. Cells were also treated with TGF-beta at a concentration of 20 ng/ml and FGF-beta at 10 ng/ml.

Sample 1: *Narcissus tazetta* bulb extract composition (a mixture of 95 parts water, 4 parts *Narcissus tazetta* bulb extract, 1 part preservative) at 0.0125 and 0.025 by weight diluted in DMEM growth media Sample 2: *Laminaria digitata* extract (a mixture of 91 parts water, 8 parts *Laminaria digitata* extract, and 1 part phenoxyethanol): 0.075% and 0.15% diluted in DMEM.

Sample 3: Hydrolyzed yeast protein composition (a mixture of 67.5 parts water, 2 parts hydrolyzed yeast protein, 30 parts glycerin, and 0.5 parts sodium benzoate) at 0.25% and 0.5% by weight diluted in Growth Media. The hydrolyzed yeast protein contains the peptide of SEQ ID No. 5.

Sample 4: Mixture containing 0.025% *Narcissus tazetta* bulb extract composition, 0.15% *Laminaria digitata* extract composition, and 0.5% hydrolyzed yeast protein containing the SIRT6 stimulating peptide of SEQ ID No. 5 diluted in Growth Media.

Samples were tested for stimulation of collagen synthesis in normal human dermal fibroblasts by adding same to wells and incubating for 3 days at 37° C. in 5% $CO_2$. Samples and control were then assayed using Vybrant® MTT Cell Proliferation Assay Kit, Life Technologies, according to kit directions. The MTT kit and Growth Media from the kit were allowed to warm to room temperature. The cell supernatants were removed and frozen for later testing with ProCollagen Peptide ELISA kit. Growth Media, 200 ul, was added to all wells containing cells. Then 20 uL of MTT reagent from the kit was added to all wells containing Growth Media. The plate was swirled to ensure thorough mixing. The plate was placed in a 37° C./5% $CO_2$ incubator for 2 hours or until cells showed purple precipitate, but no longer than 4 hours. If plates showed white precipitate, the MTT detergent in the kit was placed in the 37° C./5% $CO_2$ incubator for 10-15 minutes. Then 100 ul of MTT detergent was added to all wells and swirled to ensure mixing, taking care not to introduce bubbles into the wells. The plate was covered and stored at room temperature in the dark for 4 hours. The plate was then read on a Molecular Devices Spectramax Plate Reader at 570 nm.

The samples were also assayed using ProCollagen Peptide Elisa Kit (MK-101 from Takara Bio, Kyoto, Japan using protocol set forth in the kit.

Figure 1:
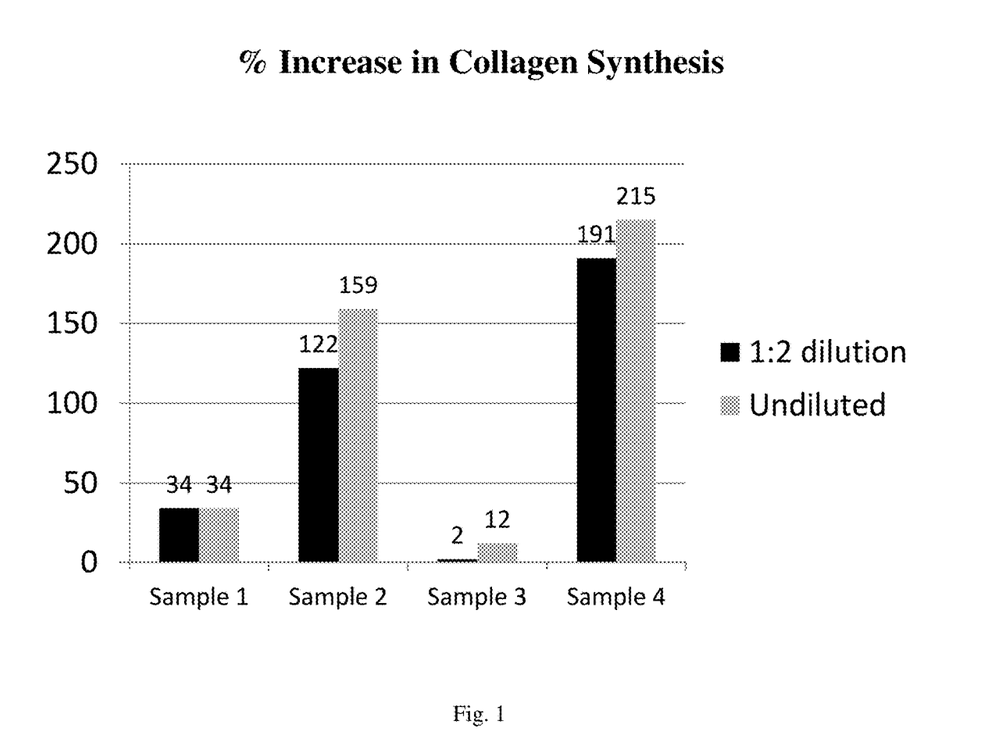
FIG. 1: illustrates that the combination of *Narcissus* extract, *Laminaria* extract and the SIRT6 peptide of the invention shows a significant increase in collagen synthesis in skin cells when compared to the ingredients tested alone and control.

The results as set forth in FIG. 1 show that the combination of *Laminaria digitata* extract, *Narcissus tazetta* bulb extract, and yeast protein extract containing the SIRT6 peptide provides an unexpected increase in collagen synthesis in normal human dermal fibroblasts.

EXAMPLE 2

SIRT6 is a member of the conserved family of sirtuin proteins which are associated with metabolism and longevity. SIRT6 is a histone 3, lysine 9 (H3K9) deacetylase and is primarily involved in DNA repair and telomere stability. The peptide of (SEQ ID No. 5) Gly-Ala-Gly-Val-Ser-Ala-Glu-$NH_2$ was tested for Sirt6 stimulating activity as follows.

Materials:
Normal Human Epidermal Keratinocytes p3
EpiLife Medium (Invitrogen)
Human Keratinocyte Growth Supplement (Invitrogen)
1× Dulbecco's Phosphate Buffered Saline (DPBS) made from:
10×DPBS (Mediatech)
Distilled, Deionized Water
Peptide of SEQ ID No. 5
Rabbit polyclonal antibody to Sirt6 (Abcam)
Alexa Fluor 488 donkey anti-rabbit IgG (H+L) (Invitrogen)
Triton-X 100 (Fisher)
Albumin, Bovine (Sigma)
Vectashield with 4',6-diamidino-2-phenylindole (DAPI) (Vector)

Figure 2:
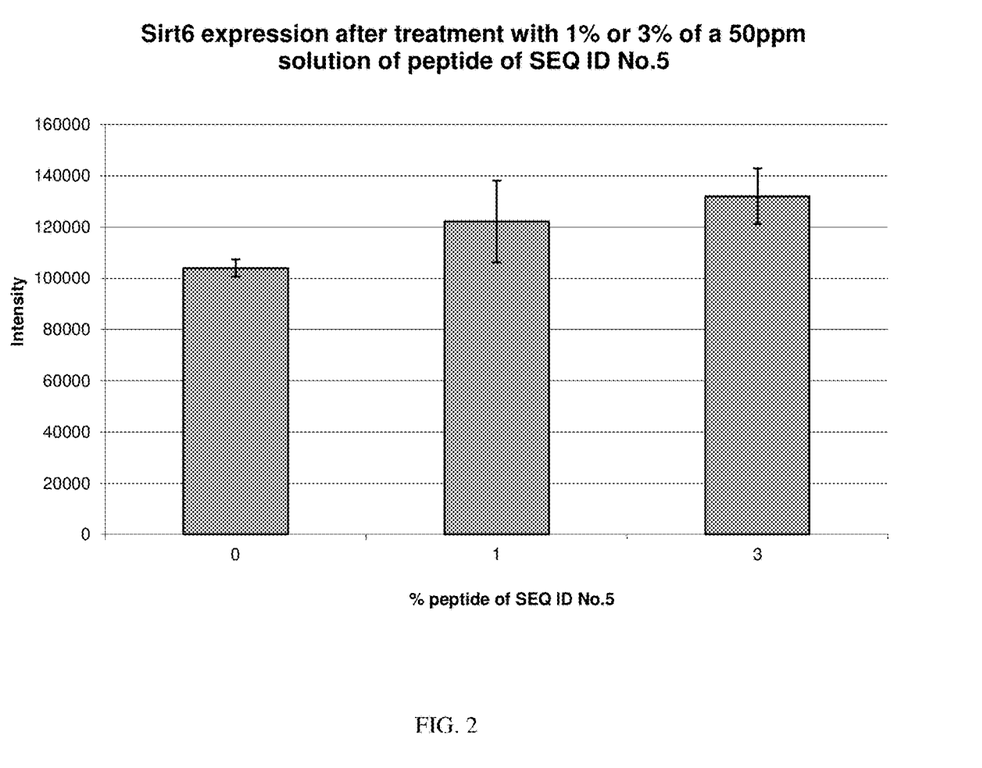
FIG. 2: illustrates the SIRT6 stimulating activity of the peptide of SEQ ID No. 5. The peptide of SEQ ID NO. 5 shows a dose dependent increase in SIRT6 expression.

Methods:
1. Cells were plated into 4 well chamber slides @ 10,000 cells/chamber and incubated at 37° C., 5% $CO_2$ & 95% humidity for 24 hours.
2. The peptide of SEQ ID No. 5 was prepared as follows:
   2.1. Dissolved 5 mg peptide in 5 ml medium to make a 1000 ppm stock solution.
   2.2. Diluted the stock solution to 50 ppm by combining 400 µl 1000 ppm stock solution with 7.6 ml medium
   2.3. Prepared a 3% of the 50 ppm solution by combining 1.5 ml 50 ppm stock with 48.5 ml medium
   2.4. Prepared a 1% of the 50 ppm solution by combining 0.5 ml 50 ppm stock with 48.5 ml medium
3. Placed treatments (500 µl per chamber) on cells for 48 h, refreshing treatments after 24 h
4. Aspirated media and replaced with the appropriate treatments. Incubated for 1 & 6 hours.
5. Performed immunohistochemistry on the cells Immunohistochemistry
6. Prepared Wash Buffer (0.2% Triton X-100):
   6.1. Add 1 mL of Triton X-100 to 499 ml of 1×PBS
7. Prepared Block Solution (1%/10 mg/ml BSA)
   7.1. Added 5 g of BSA into a final volume of 500 ml of 1×PBS
8. Aliquoted into 50 ml conical tubes and stored at −20° C.
9. Fixed cells with methanol
   9.1. Added 500 µL of ice-cold Methanol to each designated well
   9.2. Incubated for 10 min at −20° C.
10. Washed wells with 500 µL X-100 wash buffer for 5 min at room temperature
11. Added 500 µL of 1% BSA Block Solution to each well and incubate at RT for 30 min
12. All antibody solutions were briefly centrifuged to sediment invisible aggregates before aliquot was taken for dilution
13. Prepared Rabbit Anti-human SIRT6 pAb (5 µg/mL) solution:
    12 ml of 1% BSA Block
    46 µl of Sirt6 pAB
14. Removed Block solution and add 350 µL of the specified primary antibody solution to the wells
15. Incubated overnight, in a humidified chamber, at 4° C.
16. Removed all primary antibody solution
17. Washed wells 3 times with 500 µL X-100 wash buffer for 5 min each
18. Added 500 µL of 1% BSA block solution to each well and incubated at room temperature for 15 min
    The following steps were performed in the dark
19. Prepared Donkey Anti-goat 488 working solution:
    12 mL of 1% BSA Block Solution
    24 µl of Donkey Anti-rabbit IgG (H+L) Alexa Fluor® 488 (1:500 or 4 µg/mL)
20. Removed block solution and add 300 µL of Alexa Fluor solution to all wells
21. Incubated at room temperature for 1 hour
22. Removed Alexa Fluor solution
23. Washed wells 3 times with 500 µL wash buffer for 5 min.
24. Removed the top piece of the microscope slide (i.e. the chambers) to enable placement of coverslip for microscopy
25. Applied one drop of Vectashield Mounting Medium w/ DAPI to each well of the slide
26. Placed a cover slip on the slide avoiding air bubbles
27. Nail polish was applied around the cover slip border and allowed to air dry
28. Slide was placed on Whatman filter paper and wrapped with aluminum foil to protect from light and stored at −20° C. in the dark until images were captured
29. The following exposure times were used unless otherwise noted
    29.1.1. SIRT6=6 milliseconds
    29.1.2. DAPI=1 milliseconds
30. One drop of Antifade/Glycerol was then added to each well followed by cover slip The results are set forth in FIG. 2, and show a dose dependent increase in SIRT6 expression.

EXAMPLE 3

*Laminaria digitata* extract was tested for SIRT3 expression as follows:

NHEK were cultured and harvested at either the $2^{nd}$ or $3^{rd}$ passage. They were subcultivated with EpiLife Media (Invitrogen) containing growth supplements.

Cells were treated with *Laminaria digitata* extract for 48 hours at concentrations of 0.1% and 0.2%. Also run were blanks, untreated cells, and the Sirt3 standard. After treatment, the cells were harvested by trypsinization and collected by centrifugation. Cell pellets were then lysed with CytoBuster (Novagen) containing 1% protease inhibitor cocktail and 5 mM EDTA (Pierce) followed by homogenization for 30 seconds with a mini-pestle in a microfuge tube. After centrifugation (5000×g, 5 minutes), the supernatants were assayed for protein concentration by the BCA test for protein concentration (Pierce). Western blot analysis was performed on 3 ugs of protein from each sample. The reagents of the ATP Lite Kit (Perkin Elmer) were prepared as directed in the manufacturer's instructions. Cells were washed with DPBS and 50 µl of lysis buffer were added to each well. The plate was placed on the shaker for 5 min. 50 µl of substrate solution was added to each well. The plate was placed in the luminometer and dark adapted for 10 min. Then the luminescence was measured.

Figure 3:
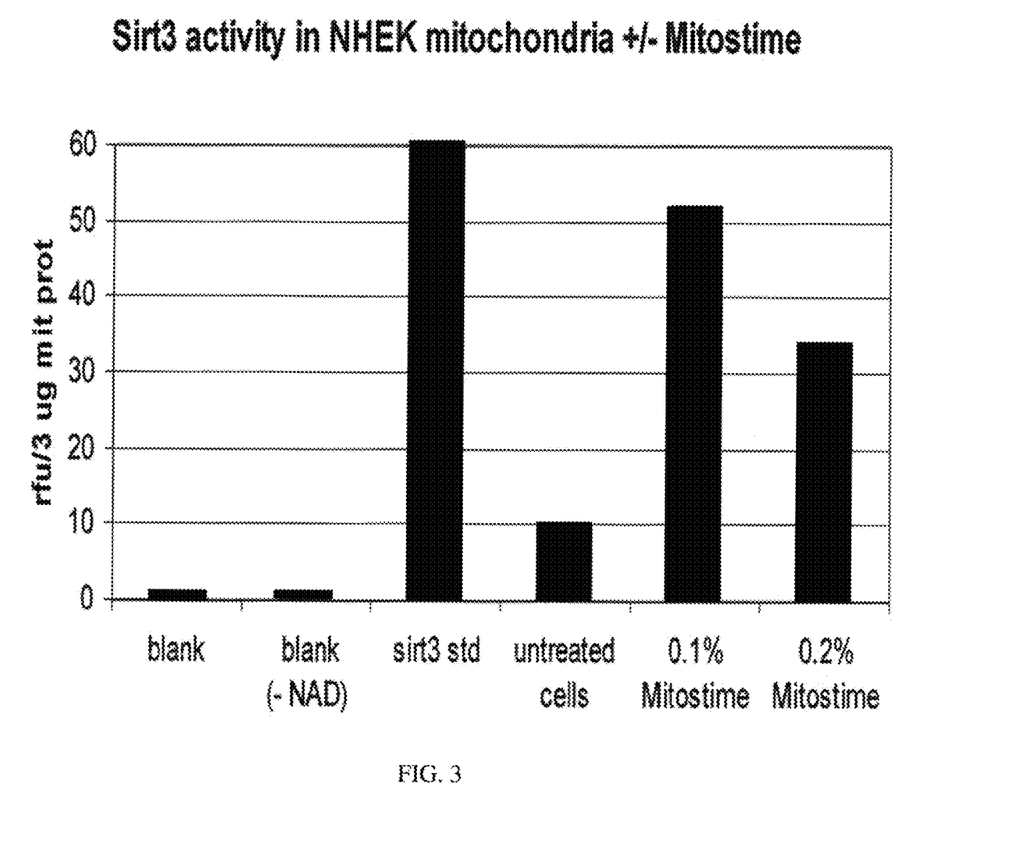
FIG. 3: illustrates the SIRT3 stimulating activity of *Laminaria digitata* extract.

Western blot analysis was performed on 4-12% gradient polyacrylamide gels electrophoresed with blue marker dye and protein standards at 180 volts, 80 mA until the blue dye had traversed the gel in MOPS SDS buffer (Invitrogen). This was followed by an electrophoretic transfer to a PVDF membrane for 1 hour at 30 volts, 180 mA. The PVDF membrane was then soaked for an hour in 5% milk (Blotto, BioRad) and then incubated overnight with shaking at 4° C. with an antibody directed against Sirt3 (Santa Cruz). After washing the membrane in TBS-T solution, a secondary HRP-IgG antibody with specificity for the primary antibody was added. Bands containing the Sirt3 protein were then visualized by a chemiluminescent reaction and imaged with a Carestream/Kodak imaging system. Actin was also probed and used as a control to normalize band intensity. Densitometry was performed with an UnScanIt software program. The results are set forth in FIG. 3 and show that *Laminaria digitata* extract at concentrations of 0.1% and 0.2% are effective in stimulating Sirt3 expression, with the 0.1% concentration being slightly more effective.

EXAMPLE 4

*Narcissus tazetta* bulb extract was measured for stimulating SIRT1 activity in keratinocytes at various concentrations.

Normal Human Keratinocytes cells were plated on a COSTAR tissue culture treated 96-well plate (Corning, N.Y.) at a concentration of $5.0 \times 10^6$ cells per plate. The cells were incubated at 37° C. and 5.0% $CO_2$ overnight. Cells were then treated with *Narcissus tazetta* bulb extract at 0, 0.0001%, 0.001%, and 0.01% concentration overnight. Resveratrol was used at 50 micromolar concentration as a positive control for SIRT1 activation. After this incubation, trichostatin A (TSA) (Biomol, Plymouth Meeting, Pa.) in PBS (phosphate buffered saline) was added to the cells, without changing the media, at a final concentration of 500 nM. The addition of TSA blocks histone deacetylation by class I and class II histone deacetylase proteins. Sirtuins are considered class III histone deacetylase proteins and are unaffected by TSA. Cells were then incubated at 37° C., 5.0% $CO_2$ for four to six hours and then assayed for acetylated histones using the Cellular Histone Acetylation Assay Kit (Cyclex, Nagano, Japan Distributed by MBL International Woburn, Mass.) using the manufacturer protocol. Cells were fixed in 95% ice-cold methanol and blocked overnight. SIRT1 activity was measured. Results showed that at concentrations greater than 0.01% *Narcissus tazetta* bulb extract, the SIRT1 activity increased by 18%. Thus *Narcissus tazetta* bulb extract stimulates SIRT1 activity.

EXAMPLE 5

A skin care composition was made as follows:

| Ingredient | Wt % |
|---|---|
| WATER\AQUA\EAU | QS100 |
| DIMETHICONE | 10.79 |
| BUTYLENE GLYCOL | 3.73 |
| VINYL DIMETHICONE/METHICONE SILSESQUIOXANE CROSSPOLYMER | 3.00 |
| GLYCERIN | 2.63 |
| POLYSORBATE 20 | 2.45 |
| POLYSILICONE-11 | 2.21 |
| LAURYL PEG-9 POLYDIMETHYLSILOXYETHYL DIMETHICONE | 1.99 |
| SILICA | 1.55 |
| LACTOBIONIC ACID | 1.00 |
| METHYL GLUCETH-20 | 0.50 |
| ACETYL GLUCOSAMINE | 0.50 |
| ETHYLHEXYLGLYCERIN | 0.50 |
| YEAST EXTRACT/SIRT6 PEPTIDE | 0.50 |
| CAPRYLYL GLYCOL | 0.40 |
| PHENOXYETHANOL | 0.38 |
| CAPRYLIC/CAPRIC TRIGLYCERIDE | 0.29 |
| SODIUM POLYACRYLATE STARCH | 0.27 |
| *HYPNEA MUSCIFORMIS* (ALGAE) EXTRACT | 0.26 |
| TITANIUM DIOXIDE (CI 77891) | 0.21 |
| CHOLESTEROL | 0.21 |
| XANTHAN GUM | 0.20 |
| CAFFEINE | 0.20 |
| *GELLIDIELA ACEROSA* (ALGAE) EXTRACT | 0.19 |
| ACRYLATES/C10-30 ALKYL ACRYLATE CROSSPOLYMER | 0.16 |
| *SIGESBECKIA ORIENTALIS* (ST. PAUL'S WORT) EXTRACT | 0.16 |
| DIPOTASSIUM GLYCYRRHIZATE | 0.15 |
| MICA | 0.14 |
| SEA WATER\AQUA MARIS\MARIS AQUA | 0.12 |
| SODIUM HYDROXIDE | 0.10 |
| TOCOPHERYL ACETATE | 0.10 |
| *COFFEA ARABICA* (COFFEE) SEED EXTRACT | 0.10 |
| DISODIUM EDTA | 0.05 |
| AMINOPROPYL ASCORBYL PHOSPHATE | 0.05 |
| ALGAE EXTRACT | 0.04 |
| *LAMINARIA DIGITATA* EXTRACT | 0.02 |
| PROPYLENE GLYCOL DICAPRYLATE | 0.02 |
| HYDROLYZED YEAST PROTEIN | 0.02 |
| GLUCOSAMINE HCL | 0.02 |
| *LAMINARIA OCHROLEUCA* EXTRACT | 0.02 |
| *PISUM SATIVUM* (PEA) EXTRACT | 0.01 |
| *BOSWELLIA SERRATA* EXTRACT | 0.01 |
| CITRIC ACID | 0.01 |
| SODIUM HYALURONATE | 0.01 |
| *CORDYCEPS SINENSIS* EXTRACT | 0.01 |
| PEARL POWDER | 0.01 |
| POLYMETHYLSILSESQUIOXANE | 0.01 |
| *PERSEA GRATISSIMA* (AVOCADO) OIL | 0.01 |
| *FUSCOPORIA OBLIQUA* EXTRACT | 0.01 |
| *CUCUMIS MELO* (MELON) FRUIT EXTRACT | 0.01 |
| *ARTEMIA* EXTRACT | 0.007 |
| *BAMBUSA VULGARIS* (BAMBOO) EXTRACT | 0.007 |
| *HELIANTHUS ANNUUS* (SUNFLOWER) SEED EXTRACT | 0.006 |
| SODIUM BENZOATE | 0.005 |
| *LAMINARIA SACCHARINA* EXTRACT | 0.005 |
| HYDROLYZED RICE PROTEIN | 0.004 |
| POTASSIUM SULFATE | 0.004 |
| POTASSIUM SORBATE | 0.002 |
| *NARCISSUS TAZETTA* BULB EXTRACT | 0.002 |
| CELLULOSE | 0.002 |
| LECITHIN | 0.001 |
| ACETYL HEXAPEPTIDE-8 | 0.0005 |

| Ingredient | Wt % |
| --- | --- |
| ERGOTHIONEINE | 0.0002 |
| HYDROGENATED STARCH HYDROLYSATE | 0.0002 |
| SACCHAROMYCES FERMENT LYSATE FILTRATE | 0.000066 |
| CUCUMIS SATIVUS (CUCUMBER) FRUIT EXTRACT | 0.000030 |
| PYRUS MALUS (APPLE) FRUIT EXTRACT | 0.000030 |
| SCUTELLARIA BAICALENSIS ROOT EXTRACT | 0.000010 |
| GOLD | 0.000002 |
| HYDROLYZED WHEAT PROTEIN | 0.000002 |

The composition was prepared by separately combining the oil phase and water phase ingredients and mixing well to emulsify. A soft cream was formed.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A method for stimulating collagen synthesis in skin cells in need of such treatment by topically applying a composition comprising at least one extract from *Laminaria* genus, at least one extract from the *Narcissus* genus, and at least one peptide of the formula (I):

$R_1$-$(AA)_n$-$X_1$-$X_2$-$X_3$-$X_4$-$X_5$-$X_6$-$(AA)_p$-$R_2$, in which $X_1$ is glycine or threonine or histidine;
$X_2$ is alanine or glutamine or glycine;
$X_3$ is glycine or asparagine or serine;
$X_4$ is valine or isoleucine or leucine;
$X_5$ is serine or aspartic acid or phenylalanine;
$X_6$ is alanine or glutamic acid or lysine; wherein
when $X_1$ is glycine, then $X_2$ is alanine and $X_3$ is glycine;
when $X_1$ is threonine, then $X_3$ is asparagine;
when $X_1$ is histidine, then $X_2$ is glycine;
AA represents any amino acid and n and p are integers between 0 and 2;
$R_1$ represents the primary amino function of the N-terminal amino acid, free or substituted by an acyl type group having either an alkyl chain from $C_{1-30}$, saturated or unsaturated, that may be an acetyl group, or an aromatic group that may be chosen from among a benzoyl, tosyl or benzyloxycarbonyl type group; and
$R_2$ represents the hydroxyl group of the carboxyl function of the C-terminal amino acid, free or substituted by a group that may be chosen from among an alkyl chain from C1-30, or an $NH_2$, NHY or NYY group with Y representing an alkyl chain from C1-4 wherein the extract from the *Laminaria* genus is present at 0.001 to 1%, the extract from *Narcissus* genus is present at 0.001 to 1.5% and the peptide is present from 0.0001 to 1%, with all percentages by weight of the total composition.

2. The method of claim 1 wherein the stimulation of collagen synthesis causes a reduction in skin laxity, a reduction in the appearance of lines or wrinkles, or both.

3. The method of claim 1 wherein the topical composition is applied once or twice per day.

4. The method of claim 1 wherein the topical composition is applied before a period of sustained rest.

5. The method of claim 1 wherein the extract from the *Laminaria* genus stimulates SIRT3activity in skin cells.

6. The method of claim 5 wherein the extract from the *Laminaria* genus is *Laminaria saccharina*.

7. The method of claim 1 wherein the extract from the *Narcissus* genus stimulates SIRT1 activity in skin cells.

8. The method of claim 7 wherein the extract from the *Narcissus* genus is *Narcissus tazetta* extract from the bulb in its dormant phase of growth.

9. The method of claim 1 wherein the peptide is selected from the group consisting of:

```
                                        (SEQ ID No. 1)
    Glu-Ile-His-Gly-Ser-Leu-Phe-Lys-NH2

(SEQ ID No. 2)
    His-Gly-Ser-Leu-Phe-Lys-NH2

(SEQ ID No. 3)
    Leu-Val-Gly-Ala-Gly-Val-Ser-Ala-NH2

(SEQ ID No. 4)
    Gly-Ala-Gly-Val-Ser-Ala-Glu (SEQ ID No. 5)
    Gly-Ala-Gly-Val-Ser-Ala-Glu-NH2

(SEQ ID No. 6)
    Thr-Gln-Asn-Ile-Asp-Glu-Leu (SEQ ID No. 7)
    Thr-Gln-Asn-Ile-Asp-Glu-Leu-NH2,
    and (SEQ ID No. 8)
    Val-Ile-Thr-Gln-Asn-Ile-Asp-Ala-NH2.
```

10. The method of claim 9 wherein the peptide is of the following formula:

```
                                        (SEQ ID No. 5)
    Gly-Ala-Gly-Val-Ser-Ala-Glu-NH2.
```

11. The method of claim 1 wherein the peptide incorporated into the composition is in the form of yeast extract with the peptide being a component of the extract.

12. The method of claim 1 wherein the extract from the *Laminaria* genus is *Laminaria digitata*.

13. The method of claim 1 wherein the extract from the *Laminaria* genus is one or more of *Laminaria digitata* or *Laminaria saccharina* and the extract from *Narcissus* is *Narcissus tazetta*.

14. The method of claim 1 wherein the skin cells are dermal fibroblasts.

* * * * *